US010314696B2

(12) United States Patent
Wulfman et al.

(10) Patent No.: US 10,314,696 B2
(45) Date of Patent: Jun. 11, 2019

(54) PROSTHETIC HEART VALVES HAVING FIBER REINFORCED LEAFLETS

(71) Applicant: Boston Scientific SciMed, Inc., Maple Grove, MN (US)

(72) Inventors: David Robert Wulfman, Minneapolis, MN (US); Thomas A. Wrobel, Long Lake, MN (US); Crystal Marie Anderson-Cunanan, San Jose, CA (US); Joseph Thomas Delaney, Jr., Minneapolis, MN (US); Patrick Willoughby, Shoreview, MN (US); Mark W. Boden, Harrisville, RI (US); Peter G. Edelman, Maple Grove, MN (US); Michael Eppihimer, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 332 days.

(21) Appl. No.: 15/082,382

(22) Filed: Mar. 28, 2016

(65) Prior Publication Data
US 2016/0296323 A1 Oct. 13, 2016

Related U.S. Application Data

(60) Provisional application No. 62/145,380, filed on Apr. 9, 2015.

(51) Int. Cl.
*A61F 2/24* (2006.01)
*A61L 27/16* (2006.01)
(Continued)

(52) U.S. Cl.
CPC .......... *A61F 2/2412* (2013.01); *A61F 2/2415* (2013.01); *A61L 27/16* (2013.01);
(Continued)

(58) Field of Classification Search
CPC ..................................................... A61F 2/2412
See application file for complete search history.

(56) References Cited

U.S. PATENT DOCUMENTS

| 4,016,714 A | 4/1977 | Crandall |
| 4,340,091 A | 7/1982 | Davis et al. |
| (Continued) | | |

FOREIGN PATENT DOCUMENTS

| CN | 1449266 | 10/2003 |
| CN | 1874799 | 12/2006 |
| (Continued) | | |

OTHER PUBLICATIONS

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).
(Continued)

*Primary Examiner* — Lee E Sanderson
*Assistant Examiner* — Michael C Romanowski
(74) *Attorney, Agent, or Firm* — Pauly, DeVries Smith & Deffner LLC (57) ABSTRACT

A prosthetic heart valve leaflet includes a plurality of electrospun fibers at least partially embedded in a polymer matrix. The plurality of fibers includes a first polyisobutylene urethane copolymer having a first predetermined weight average percentage of hard segment portions and the polymer matrix includes a second polyisobutylene urethane copolymer having a second predetermined weight average percentage of the hard segment portions, wherein the first predetermined weight average percentage of the hard segment portions is greater than the second predetermined weight average percentage of the hard segment portions.

11 Claims, 6 Drawing Sheets

(51) Int. Cl.
  *A61L 27/18* (2006.01)
  *A61L 27/52* (2006.01)
  *A61L 27/34* (2006.01)
(52) U.S. Cl.
  CPC .............. *A61L 27/18* (2013.01); *A61L 27/34* (2013.01); *A61L 27/52* (2013.01); *A61L 2400/12* (2013.01); *A61L 2420/02* (2013.01); *A61L 2420/08* (2013.01); *A61L 2430/20* (2013.01)

(56) References Cited

U.S. PATENT DOCUMENTS

| | | | |
|---|---|---|---|
| 4,753,652 | A | 6/1988 | Langer et al. |
| 5,296,292 | A | 3/1994 | Butters |
| 5,674,286 | A | 10/1997 | D'Alessio et al. |
| 5,679,299 | A | 10/1997 | Gilbert et al. |
| 5,688,597 | A | 11/1997 | Kohno |
| 5,740,051 | A | 4/1998 | Sanders, Jr. et al. |
| 6,165,215 | A | 12/2000 | Rottenberg et al. |
| 6,726,715 | B2 | 4/2004 | Sutherland |
| 6,953,332 | B1 | 10/2005 | Kurk et al. |
| 7,335,264 | B2 | 2/2008 | Austin et al. |
| 7,517,353 | B2 | 4/2009 | Weber |
| 7,521,296 | B2 | 4/2009 | Wood et al. |
| 7,615,335 | B2 | 11/2009 | Shelnut et al. |
| 7,786,670 | B2 | 8/2010 | Veres et al. |
| 7,988,900 | B2 | 8/2011 | Beith et al. |
| 8,324,290 | B2 | 12/2012 | Desai et al. |
| 8,361,144 | B2 | 1/2013 | Fish et al. |
| 8,590,747 | B2 | 11/2013 | Keller et al. |
| 8,845,580 | B2 | 9/2014 | Gellman et al. |
| 8,864,816 | B2 | 10/2014 | Flanagan et al. |
| 9,056,006 | B2 | 6/2015 | Edelman et al. |
| 9,074,318 | B2 | 7/2015 | Chou et al. |
| 9,255,929 | B2 | 2/2016 | Jiang et al. |
| 9,554,900 | B2 | 1/2017 | Bruchman et al. |
| 9,737,400 | B2 | 8/2017 | Fish et al. |
| 9,814,572 | B2 | 11/2017 | Edelman et al. |
| 9,944,529 | B2 | 4/2018 | Zhang et al. |
| 2001/0025196 | A1 | 9/2001 | Chinn et al. |
| 2002/0082689 | A1 | 6/2002 | Chinn et al. |
| 2003/0055496 | A1 | 3/2003 | Cai et al. |
| 2003/0078652 | A1 | 4/2003 | Sutherland et al. |
| 2003/0097175 | A1 | 5/2003 | O'connor et al. |
| 2003/0171802 | A1 | 9/2003 | Wilder et al. |
| 2003/0183982 | A1 | 10/2003 | Jansen et al. |
| 2004/0015233 | A1 | 1/2004 | Jansen et al. |
| 2004/0022939 | A1 | 2/2004 | Kim et al. |
| 2005/0228486 | A1 | 10/2005 | Flagle et al. |
| 2006/0190074 | A1 | 8/2006 | Hill et al. |
| 2007/0118210 | A1 | 5/2007 | Pinchuk et al. |
| 2007/0144124 | A1 | 6/2007 | Schewe et al. |
| 2007/0232169 | A1 | 10/2007 | Strickler et al. |
| 2007/0254005 | A1 | 11/2007 | Pathak et al. |
| 2008/0045420 | A1 | 2/2008 | Karagianni et al. |
| 2009/0041978 | A1 | 2/2009 | Sogard et al. |
| 2009/0054969 | A1 | 2/2009 | Salahieh et al. |
| 2009/0117334 | A1 | 5/2009 | Sogard et al. |
| 2009/0149673 | A1 | 6/2009 | Zhang et al. |
| 2009/0155335 | A1 | 6/2009 | O'shaughnessey et al. |
| 2009/0324679 | A1 | 12/2009 | Ippoliti et al. |
| 2010/0023104 | A1 | 1/2010 | Desai et al. |
| 2010/0179298 | A1 | 7/2010 | Faust et al. |
| 2010/0249922 | A1 | 9/2010 | Li et al. |
| 2011/0022160 | A1 | 1/2011 | Flanagan et al. |
| 2011/0208299 | A1 | 8/2011 | Marissen et al. |
| 2011/0305898 | A1 | 12/2011 | Zhang et al. |
| 2012/0258313 | A1 | 10/2012 | Wen et al. |
| 2013/0150957 | A1 | 6/2013 | Weber et al. |
| 2013/0211508 | A1 | 8/2013 | Lane et al. |
| 2013/0274874 | A1 | 10/2013 | Hammer et al. |
| 2014/0005771 | A1 | 1/2014 | Braido et al. |
| 2014/0005772 | A1* | 1/2014 | Edelman ............... A61F 2/2412 623/2.17 |
| 2014/0018440 | A1 | 1/2014 | Boden et al. |
| 2014/0088716 | A1 | 3/2014 | Zubok et al. |
| 2014/0163671 | A1 | 6/2014 | Bruchman et al. |
| 2014/0180402 | A1 | 6/2014 | Bruchman et al. |
| 2014/0322512 | A1 | 10/2014 | Pham et al. |
| 2015/0005869 | A1 | 1/2015 | Soletti et al. |
| 2015/0182332 | A1 | 7/2015 | Edelman et al. |
| 2015/0265392 | A1 | 9/2015 | Flanagan et al. |
| 2016/0296322 | A1 | 10/2016 | Edelman |
| 2016/0296325 | A1 | 10/2016 | Edelman |
| 2017/0000610 | A1 | 1/2017 | Eppihimer et al. |
| 2017/0014227 | A1 | 1/2017 | Boden et al. |
| 2017/0071729 | A1 | 3/2017 | Wrobel |
| 2017/0156854 | A1 | 6/2017 | Hammer |
| 2017/0231758 | A1 | 8/2017 | Bruchman et al. |
| 2017/0266350 | A1 | 9/2017 | Jiang et al. |
| 2017/0333185 | A1 | 11/2017 | Weber et al. |
| 2018/0049869 | A1 | 2/2018 | Edelman et al. |
| 2018/0303972 | A1 | 10/2018 | Delaney, Jr. et al. |

FOREIGN PATENT DOCUMENTS

| | | |
|---|---|---|
| CN | 101437663 | 5/2009 |
| CN | 101505723 | 8/2009 |
| CN | 101690683 | 4/2010 |
| CN | 103628147 | 3/2014 |
| CN | 104203151 | 12/2014 |
| JP | H0654868 | 3/1994 |
| WO | 0224119 | 3/2002 |
| WO | 02074201 | 9/2002 |
| WO | 2005039664 | 5/2005 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |

OTHER PUBLICATIONS

Alferiev, Ivan et al., "Prevention of polyurethane valve cusp calcification with covalently attached bisphosphonate diethylamino moieties," J Biomed Mater Res 66A: 385-395, 2003 (11 pages).
Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).
Barkoula, Nektaria-Marianthi et al., "Processing of Single Polymer Composites Using the Concept of Constrained Fibers," Polymer Composites, 2005, 26: p. 114-120 (7 pages).
Bastiaansen, Cees W. et al., "Melting Behavior of Gelspun-Drawn Polyolefins," Makromol. Chem., Macromol. Symp., 1989. 28: p. 73-84 (12 pages).
Bates, Frank S. et al., "Multiblock Polymers: Panacea or Pandora's Box?," Science, 2012, 336:434-440 (7 pages).
Bernacca, Gillian M. et al., "Mechanical and morphological study of biostable polyurethane heart valve leaflets explanted from sheep," J Biomed Mater Res 61:138-145, 2002 (8 pages).
Bhattacharyya, D. et al., "Polyamide 6 single polymer composites," eXPRESS Polym. Lett., 2009. 3(8): p. 525-532 (8 pages).
Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).
Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

(56) References Cited

OTHER PUBLICATIONS

De Yoreo, James J. et al., "Principles of Crystal Nucleation and Growth," Biomineralization, Mineral Soc. Am., Washington, DC, 2003, pp. 57-93 (37 pages).

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).

Duhovic, Miro P. et al., "Polyamide 66 polymorphic single polymer composites," Open Macromol. J., 2009. 3: p. 37-40. (4 pages).

Fakirov, Stoyko "Nano- and Microfibrillar Single-Polymer Composites: A Review," Macromol. Mater. Eng., 2013. 298(1): p. 9-32 (24 pages).

Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).

File History for U.S. Appl. No. 13/932,968.

File History for U.S. Appl. No. 14/656,044.

"First Office Action," for Chinese Patent Application No. 201380044842.0 dated Dec. 18, 2015 (15 pages) with English Translation.

Généreux, Philippe et al., "Vascular Complications After Transcatheter Aortic Valve Replacement: Insights from the Partner Trial," J Am Coll Cardiol. 2012;60(12):1043-1052 (10 pages).

"Glycosaminoglycan," Wikipedia, posted on or before Oct. 16, 2004, retrieved Feb. 13, 2014, http://en.wikipedia.org/wiki/Glycosaminoglycan, 6 pages.

Gong, Ying et al., "Polyamide single polymer composites prepared via in situ anionic polymerization of ε-caprolactam," Composites, Part A, 2010. 41A(8): p. 1006-1011 (6 pages).

Gong, Ying et al., "Single polymer composites by partially melting recycled polyamide 6 fibers: preparation and characterization," J. Appl. Polym. Sci., 2010. 118(6): p. 3357-3363 (7 pages).

Goyal, R. K. et al., "High performance polymer composites on PEEK reinforced with aluminum oxide," J. Appl. Polym. Sci., 2006. 100(6): p. 4623-4631 (9 pages).

Han, Dong K. et al., "In vivo biostability and calcification-resistance of surface-modified PU-PEO-SO3," Journal of Biomedical Materials Research, vol. 27, 1063-1073, 1993 (11 pages).

Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).

Hine, P.J. et al., "Hot compaction of woven nylon 6,6 multifilaments," J. Appl. Polym. Sci., 2006. 101(2): p. 991-997 (7 pages).

Hine, P.J. et al., "Hot Compaction of Woven Poly(ethylene terephthalate) Multifilaments," J. Appl. Polym. Sci., 2004. 91(4): p. 2223-2233 (11 pages).

Hine, P.J. et al., "Hybrid carbon fibre/nylon 12 single polymer composites," Composites Part A: Applied Science and Manufacturing 65 (2014) (17 pages).

"International Preliminary Report on Patentability," for International Application No. PCT/US2013/048976 dated Jan. 6, 2015 (9 pages).

"International Search Report & Written Opinion," for International Application No. PCT/US2013/048976, dated Nov. 19, 2013 (20 pages).

Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).

Kaflon-Cohen, Estelle et al., "Microstructure and nematic transition in thermotropic liquid crystalline fibers and their single polymer composites," Polym. Adv. Technol., 2007. 18(9): p. 771-779 (9 pages).

Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).

Khondker, O.A. et al., "Fabrication and mechanical properties of aramid/nylon plain knitted composites," Composites Part A: Applied Science and Manufacturing, 2004. 35(10): p. 1195-1205 (11 pages).

Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).

Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).

"Liquid-Crystal Polymer," Wikipedia, the Free Encyclopedia <http://en/wikipedia.org/wiki/Liquid-crystal_polymer>, retrieved Jun. 2, 2016 (3 pages).

Liu, et al., "Effect of fiber orientation on the stress distribution within a leaflet of a polymer composite heart valve in the closed position," J of Biomedichanics, 2007, 40:1099-1106 (8 pages).

Maity, J. et al., "Homocomposites of chopped fluorinated polyethylene fiber with low-density polyethylene matrix," Mater. Sci. Eng., A, 2008. A479(1-2): p. 125-135 (11 pages).

Matabola, K. P. et al., "Single polymer composites: a review," Journal of Materials Science, 2009. 44(23): p. 6213-6222 (10 pages).

Medeiros Araujo, Thiago et al., "Liquid crystalline single-polymer short-fibers composites," Composite Interfaces, 2013. 20(4): p. 287-298 (12 pages).

Ohri, Rachit et al., "Hyaluronic acid grafting mitigates calcification of glutaraldehyde-fixed bovine pericardium," J Biomed Mater Res 70A: 328-334, 2004 (7 pages).

Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).

Sun, Xiaoli et al., "α and β Interfacial Structures of the iPP/PET Matrix/Fiber Systems," Macromolecules, 2007. 40(23): p. 8244-8249 (6 pages).

Vick, Linda W. et al., "Hot compaction and consolidation of polycarbonate powder," Polym. Eng. Sci., 1998. 38(11): p. 1824-1837 (14 pages).

Wang, Qiang et al., "A novel small animal model for biocompatibility assessment of polymeric materials for use in prosthetic heart valves," J Biomed Mater Res 93A: 442-453, 2010 (12 pages).

Wang, Qiang et al., "In-Vivo Assessment of a Novel Polymer (SIBS) Trileaflet Heart Valve," J Heart Valve Dis, Jul. 2010, 19(4):499-505 (7 pages).

Ward, I.M. et al., "Developments in oriented polymers," Plastics, Rubber and Composites, 2004. 33(5): p. 189-194 (6 pages).

Ward, I.M. et al., "Novel composites by hot compaction of fibers," Polym. Eng. Sci., 1997. 37(11): p. 1809-1814 (6 pages).

Wheatley, et al., "Polyurethane: material for the next generation of heart valve prostheses?," Eur J Cardio-Thoracic Surg, 2000, 17:440-448 (11 pages).

Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).

Yao, Jian et al., "High Strength and High Modulus Electrospun Nanofibers," Fibers 2014; 2:158-187 (30 pages).

Yeh, Shiou-Bang et al., "Modification of Silicone Elastomer with Zwitterionic Silane for Durable Antifouling Properties," Langmuir 2014, 30, 11386-11393 (8 pages).

Zhang, Baoyan et al., "Studies of Novel Segmented Copolyether Polyurethanes," Eur. Polym. J., vol. 34, No. 3-4, pp. 571-575 (1998) (5 pages).

Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).

Zhao, Zeng Hua et al., "Research development of single polymer composite preparation," Gongcheng Suliao Yingyong, 2010. 38(2): p. 81-84, with machine translation (11 pages).

(56) References Cited

OTHER PUBLICATIONS

Berkland, Cory et al., "Controlling surface nano-structure using flow-limited field-injection electrostatic spraying (FFESS) of poly(D,L-lactide-co-glycolide)," Biomaterials (2004) 25: 5649-5658.
Fabreguette, et al., "X-ray mirrors on flexible polymer substrates fabricated by atomic layer deposition," Thin Solid Films 515: 7177-7180 (2007).
Fabreguette, Francois H. et al., "Ultrahigh x-ray reflectivity from W/Al2O3 multilayers fabricated using atomic layer deposition," Applied Physics Letters 88: 013166 (2006), 3 pages.
"Final Office Action," for U.S. Appl. No. 15/193,794 dated May 23, 2018 (12 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).
Hass, D. D. et al., "Reactive vapor deposition of metal oxide coatings," Surface and Coatings Technology 146-147 (2001) 85-93.
"International Preliminary Report on Patentability," for PCT Application No. PCT/US2016/050691 dated Mar. 29, 2018 (9 pages).
"International Search Report and Written Opinion," for PCT Application No. PCT/US2017/032656 dated Jul. 21, 2017 (16 pages).
Jen, Shih-Hui et al., "Critical tensile and compressive strains for cracking of al2o3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185.
"Non-Final Office Action," for U.S. Appl. No. 15/082,239 dated May 16, 2018 (34 pages).
"Non-Final Office Action," for U.S. Appl. No. 15/257,211 dated Apr. 10, 2018 (39 pages).
"Notification of Patent Reexamination," for Chinese Patent Application No. 201380044842.0 dated Feb. 7, 2018 (12 pages) with English summary.
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Non-Final Office Action," for U.S. Appl. No. 15/193,794, dated Mar. 14, 2018, filed Apr. 16, 2018 (8 pages).
"Response to Non-Final Office Action," for U.S. Appl. No. 15/257,211, dated Apr. 10, 2018, filed Jun. 18, 2018 (10 pages).
"Response to Non-Final Office Action," for U.S. Appl. No. 15/082,239, dated May 16, 2018, filed Jun. 19, 2018 (13 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967.
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"Non-Final Office Action," for U.S. Appl. No. 15/193,794 dated Mar. 14, 2018 (14 pages).
"Non-Final Office Action," for U.S. Appl. No. 15/193,794 dated Nov. 6, 2017 (32 pages).
"Response to Non-Final Office Action," for U.S. Appl. No. 15/193,794, dated Nov. 6, 2017, filed Feb. 13, 2018 (7 pages).
"Decision of Final Rejection," for China Patent Application No. 201380044842.0, dated Apr. 7, 2017 (18 pages) with Summary.
"Non-Final Office Action," for U.S. Appl. No. 14/656,044 dated Mar. 17, 2017 (34 pages).
"Response to Non-Final Office Action," for U.S. Appl. No. 14/656,044 dated Mar. 17, 2017, filed Jun. 8, 2017 (11 pages).
Final Office Action for U.S. Appl. No. 15/257,211 dated Jul. 26, 2018 (13 pages).
Non-Final Office Action for U.S. Appl. No. 15/082,293 dated Jul. 11, 2018 (41 pages).
Response to Communication Pursuant to Rules 161(1) and 162 EPC for European Patent Application No. 16736720.0 filed with the EPO Jul. 12, 2018 (12 pages).
Response to Final Office Action for U.S. Appl. No. 15/193,794, dated May 23, 2018, filed Jul. 17, 2018 (10 pages).
Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.
Cacciola, G. et al., "A Three-Dimensional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.
"Communication Pursuant to Article 94(3) EPC," for European Patent Application No. 13739321.1 dated Sep. 8, 2016 (4 pages).
"Final Office Action," for U.S. Appl. No. 14/656,044 dated Sep. 9, 2016 (17 pages).
Gallocher, "Durability Assessment of Polymer Trileaflet Heart Valves," FIU Electronic Theses and Dissertations, Paper 54, 2007 (237 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
"International Search Report and Written Opinion," for PCT/US2016/039808 dated Sep. 26, 2016 (11 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Masoumi, et al., "Trilayered Elastomeric Scaffolds for Engineering Heart Valve Leaflets," Biomaterials. Sep. 2014; 35(27):7774-7785.
"Response to Non-Final Office Action," for U.S. Appl. No. 14/656,044, dated May 20, 2016, filed Aug. 9, 2016 (11 pages).
Vesely, et al., "Micromechanics of the Fibrosa and the Ventricularis in Aortic Valve Leaflets," J Biomech. 1992 25(1):101-113.
"International Search Report and Written Opinion," for PCT Application No. PCT/US2016/041757 dated Oct. 12, 2016 (12 pages).
"International Search Report and Written Opinion," for PCT application No. PCT/US2016/050691 dated Dec. 19, 2016 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
"Response to Communication Pursuant to Article 94(3) EPC," for European Patent Application No. 13739321.1 filed with the EPO Jan. 2, 2017 (37 pages).

(56) References Cited

OTHER PUBLICATIONS

"Response to Final Office Action," for U.S. Appl. No. 14/656,044, dated Sep. 9, 2016, filed Dec. 8, 2016 (9 pages).
"Second Office Action," for Chinese Patent Application No. 201380044842.0, dated Aug. 12, 2016 (16 pages) with summary.
Tu, Qin et al., "Synthesis of Polyethylene Glycol- and Sulfobetaine-Conjugated Zwitterionic Poly(l-lactide) and Assay of its Antifouling Properties," Colloids and Surfaces B; Biointerfaces 102 (2013) 331-340 (10 pages).
Response to Communication Pursuant to Rules 161(1) and 162 EPC for European Patent Application No. 16766455.6 filed Dec. 4, 2018 (9 pages).
Final Office Action for U.S. Appl. No. 15/082,239 dated Oct. 12, 2018 (19 pages).
First Office Action for Chinese Patent Application No. 20160036250.8 dated Nov. 2, 2018 (11 pages) with English Summary.
First Office Action for Chinese Patent Application No. 201680018700.0 dated Nov. 2, 2018 (12 pages) with English Summary.
International Preliminary Report on Patentability for PCT Application No. PCT/US2017/032656 dated Nov. 29, 2018 (7 pages).
International Search Report and Written Opinion for PCT Application No. PCT/US2018/028864 dated Jul. 30, 2018 (10 pages).
Madhusha, "Difference between Fluorine and Fluoride," Aug. 9, 2017, PEDIAA.com, pp. 1-8. URL <http://pediaa.com/difference-between-fluorine-and-fluoride/> (8 pages).
Non-Final Office Action for U.S. Appl. No. 15/205,098 dated Oct. 30, 2018 (42 pages).
Non-Final Office Action for U.S. Appl. No. 15/595,176 dated Aug. 27, 2018 (30 pages).
Non-Final Office Action for U.S. Appl. No. 15/797,394 dated Sep. 26, 2018 (39 pages).
Notice of Allowance for U.S. Appl. No. 15/257,211 dated Sep. 24, 2018 (7 pages).
Response to Final Rejection dated Jul. 26, 2018, for U.S. Appl. No. 15/257,211, submitted via EFS-Web on Aug. 9, 2018, 5 pages.
Response to Non-Final Rejection dated Aug. 27, 2018, for U.S. Appl. No. 15/595,176, submitted via EFS-Web on Nov. 26, 2018, 6 pages.
Response to Non-Final Rejection dated Jul. 11, 2018, for U.S. Appl. No. 15/028,293, submitted via EFS-Web on Oct. 11, 2018, 12 pages.
Response to Final Rejection dated Oct. 12, 2018, for U.S. Appl. No. 15/082,239, submitted via EFS-Web on Dec. 17, 2018, 9 pages.

* cited by examiner

PROSTHETIC HEART VALVES HAVING FIBER REINFORCED LEAFLETS

This application claims the benefit of U.S. Provisional Application No. 62/145,380 filed Apr. 9, 2015, the contents of which are herein incorporated by reference.

TECHNICAL FIELD

The present invention relates to prosthetic heart valves having leaflets made of a fiber-reinforced composite material.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, the blood within a heart chamber can regurgitate, or leak backwards through the valve.

Valve regurgitation may be treated by replacing or repairing a diseased valve, such as an aortic valve. Surgical valve replacement is one method for treating the diseased valve, but other less invasive methods of treatments are also available to many patients. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Although prosthetic heart valves can be a remedy for a diseased valve, valve leaflets of the prosthetic heart valve can accumulate calcium deposits over time, referred to as calcification, and can experience long-term device failures such as tearing. Accordingly, there is a desire to provide heart valves having sufficient long-term chemical stability, and physical and mechanical properties.

SUMMARY

Prosthetic heart valves provided herein can have a structure adapted to retain functionality during the life of the patient with adequate chemical, physical and mechanical properties. In various cases, prosthetic heart valves provided herein include leaflets made of fiber-reinforced composite materials.

In Example 1, a prosthetic heart valve leaflet includes a fibrous composite material composed of a plurality of electrospun fibers at least partially embedded in a polymer matrix. The prosthetic heart valve leaflet can be characterized by the polymer matrix comprising a polyisobutylene urethane copolymer and the electrospun fibers comprising a polyurethane, fluoropolymer, polyester or a tri-block polymer.

In Example 2, the prosthetic heart valve leaflet of Example 1, wherein the electrospun fibers comprise a polyisobutylene urethane (PIB-PUR) copolymer, polytetrafluoroethylene (PTFE), a polyethylene terephthalate (PET), or a poly(styrene-isobutylene-styrene) (SIBS) tri-block polymer.

In Example 3, the prosthetic heart valve of Examples 1 or 2, wherein the plurality of electrospun fibers comprise a first polyisobutylene urethane copolymer having a first predetermined weight average percentage of hard segment portions and the polymer matrix comprises a second polyisobutylene urethane copolymer having a second predetermined weight average percentage of the hard segment portions, the first and second polyisobutylene urethane copolymers each comprising soft segment portions, characterized by the first predetermined weight average percentage of the hard segment portions being greater than the second predetermined weight average percentage of the hard segment portions.

In Example 4, the prosthetic heart valve leaflet of one of Examples 1-3, wherein the polymer matrix includes a polyisobutylene urethane copolymer having a durometer from about 60 A to about 55 D shore hardness or in some cases about 55 D. In some embodiments, the plurality of electrospun fibers can include a polymeric material having a tensile strength from 20 MPa to 45 MPa, or in some cases at least 49 MPa. In some embodiments, the polymer matrix can have a tensile strength from 20 MPa to 45 MPa, or in some cases about 44 MPa.

In Example 5, the prosthetic heart valve leaflet of one of Examples 1-4, wherein the prosthetic heart valve leaflet is one of at least two prosthetic heart valve leaflets coupled to the tubular body of a prosthetic heart valve.

In Example 6, the prosthetic heart valve leaflet of Example 5, wherein the first and second hard segment portions are each prepared from a methylene diisocyanate and a butane diol.

In Example 7, the prosthetic heart valve leaflet of Example 5 or Example 6, wherein the soft segment portions are prepared from a monomer of a polyisobutylene diol or a polyisobutylene diamine.

In Example 8, the prosthetic heart valve leaflet of one of Examples 5-7, wherein the soft segment portions further includes at least a polyether, a fluorinated polyether, a fluoropolymer, a polyester, a polyacrylate, a polymethacrylate, a polysiloxane, a fluorinated polysiloxane, or a polycarbonate.

In Example 9, the prosthetic heart valve leaflet of one of Examples 5-8, wherein the first polyisobutylene urethane copolymer includes a weight average percentage of the hard segment ranging between about 40 wt % to about 60 wt % and a weight average percent of the soft segment of about 40 wt % to about 60 wt %.

In Example 10, the prosthetic heart valve leaflet of one of Examples 5-8, wherein the second polyisobutylene urethane copolymer includes a weight average percentage of the hard segment ranging between about 30 wt % to about 40 wt % and a weight average percent of the soft segment of about 60 wt % to about 70 wt %.

In Example 11, the prosthetic heart valve leaflet of one of Examples 1-10, further including a hydrogel coating on a surface of the leaflet.

In Example 12, the prosthetic heart valve leaflet of Example 11, wherein the hydrogel coating includes polyethylene glycol (PEG).

In Example 13, the prosthetic heart valve leaflet of one of Examples 1-12, wherein a first portion of the plurality of electrospun fibers have a first predetermined orientation and a second portion of the plurality of electrospun fibers have a second predetermined orientation, wherein the first predetermined orientation is different than the second predetermined orientation.

In Example 14, the prosthetic heart valve leaflet of one of Examples 1-13, wherein the polyisobutylene urethane copolymer includes hard segment portions, wherein each hard segment portion is prepared from a methylene diisocyanate (MDI) and a butane diol (BD), preferably wherein the polyisobutylene urethane copolymer is prepared using a mole ratio of MDI/(BD+SS) of about 1.

In Example 15, a method for making a prosthetic heart valve leaflet of one of Examples 1-14 that includes disposing the plurality of electrospun fibers onto a mandrel and disposing a layer of the polymer matrix onto the mandrel. In some embodiments, disposing the layer of the polyisobutylene urethane copolymer can include using a dip coating process, compression molding process or a spraying process. In some embodiments, Example 15 can further include applying a hydrogel coating that includes polyethylene glycol. In some embodiments, the hydrogel coating can include heparin.

BRIEF DESCRIPTION OF THE DRAWINGS

FIGS. 3A and 3B are views of an exemplary leaflet provided herein composed of a composite material.

DETAILED DESCRIPTION

Figure 1:
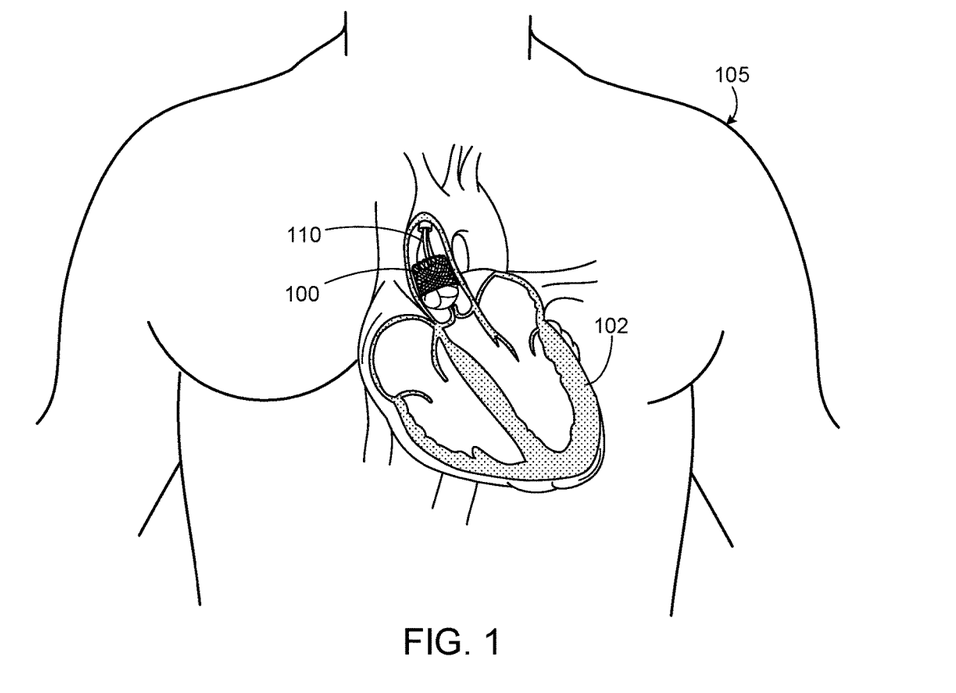
FIG. 1 is an illustration of an exemplary prosthetic heart valve provided herein within a human anatomy.

FIG. 1 is an illustration of a prosthetic heart valve 100 provided herein within a heart 102 of a human body 105. The heart has four heart valves: a pulmonary valve, a tricuspid valve, an aortic valve and a mitral valve. The heart valves allow blood to pass through the heart and into major blood vessels connected to the heart, for example, the aorta and pulmonary artery. Prosthetic heart valve 100 of FIG. 1 is an aortic prosthetic heart valve that can be surgically implanted or delivered through blood vessels using a delivery device or catheter 110. The delivery catheter 110 can be inserted into a femoral, subclavian, or an aortic incision during a transcatheter aortic valve replacement (TAVR) procedure. Once inserted, the delivery catheter 110 can deliver the prosthetic heart valve 100 to the desired location within the anatomy and release the implantable heart valve 100 at a desired implantation site. Although FIG. 1 shows prosthetic heart valve 100 replacing an aortic valve, in some cases, prosthetic heart valve 100 can be a replacement for another type of heart valve (e.g., a mitral valve or a tricuspid valve).

Figure 2:
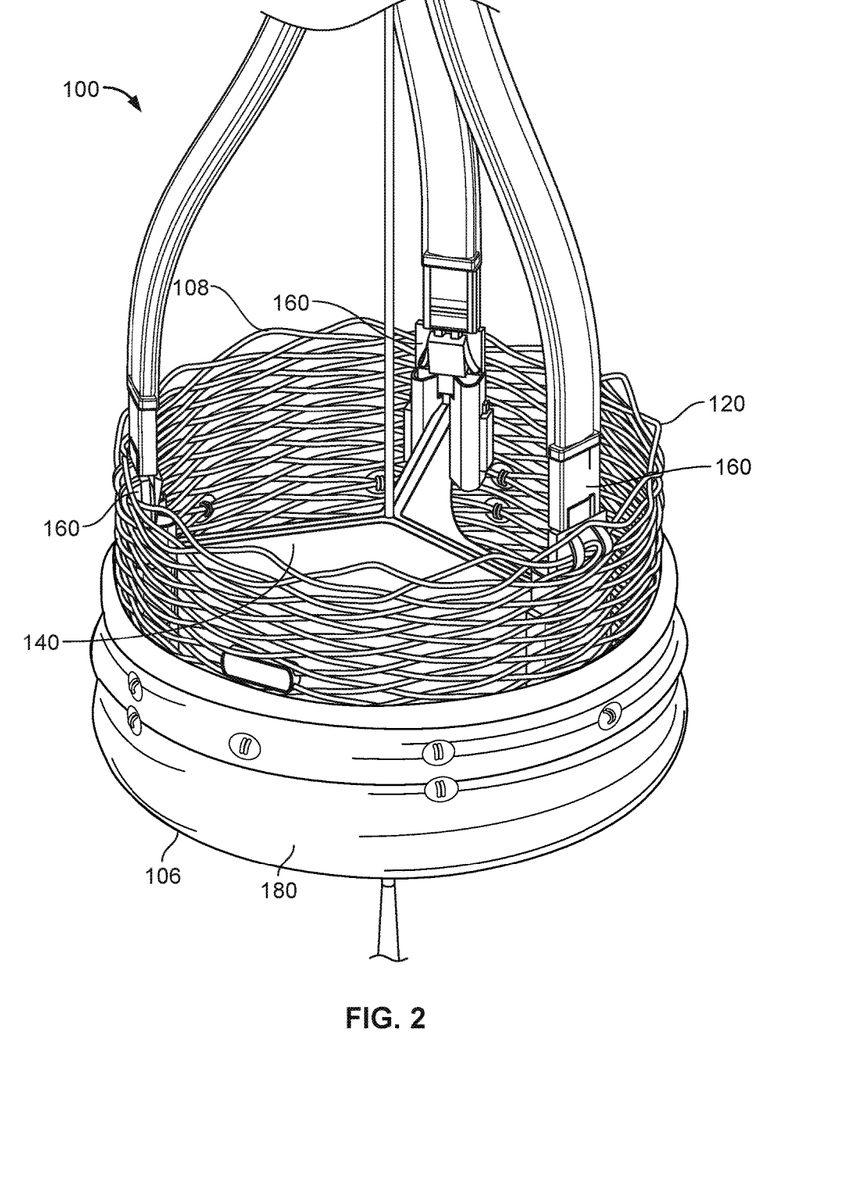
FIG. 2 is an enlarged view of the prosthetic heart valve of FIG. 1.

FIG. 2 provides a close up view of the prosthetic heart valve 100 of FIG. 1. Prosthetic heart valve 100 has a substantially tubular body 120, three leaflets 140, anchor elements 160 and a tubular seal 180. Tubular body 120 can be a radially expandable member, e.g. annular frame or stent, having an annular cavity. As shown in FIG. 2, heart valve 100 can have heart valve leaflets 140 coupled to tubular body 120 within the annular cavity. Three anchor elements 160 positioned within the annular cavity of tubular body 120 can each secure the heart valve leaflets 140 to the tubular body 120. Each anchor element 160 can be coupled to the tubular body 120 with fasteners and coupled to the leaflets 140 with a clamping element. Tubular seal 180 can be disposed about a portion of the tubular body 120. In particular, tubular seal 180 can have an outflow end portion 108 disposed about an outer surface of the tubular body 120 to restrict blood flow around the leaflets. The tubular seal 180 can also have an inflow end portion 106 secured to bottom edges of the leaflets 140.

Prosthetic heart valve 100 can be made of various materials. In some cases, at least a portion of prosthetic heart valve 100, for example, the leaflets 140 or a portion of the tubular body 120, can be made of various synthetic materials. In some cases, prosthetic heart valve 100 can be made entirely of synthetic materials. The synthetic materials of prosthetic heart valve 100 can include polymeric materials, metals, ceramics, and combinations thereof. In some cases, synthetic materials of the prosthetic heart valve 100 can include a composite material composed of at least two constituent materials with different physical, mechanical and/or chemical properties.

In some cases, at least a portion of the leaflet 140 can be made from tissue obtained from an animal, e.g., a pig or a cow. In some cases, for example, leaflets 140 can be partially made from bovine pericardium or porcine tissue.

Figure 3A:
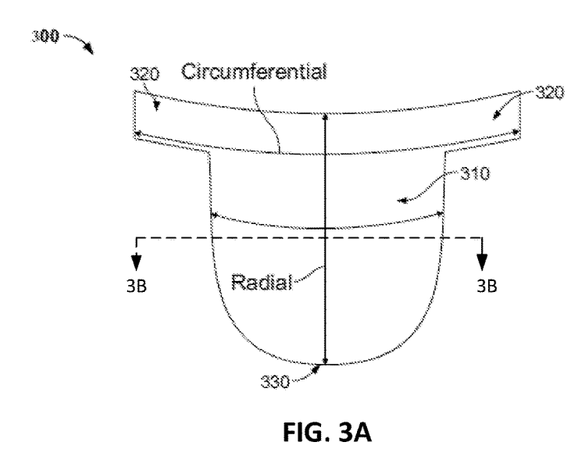
FIG. 3A shows a plan view of the exemplary leaflet.

FIG. 3A shows an exemplary prosthetic heart valve leaflet 300 described herein. As shown, leaflet 300 can include a body portion 310 (which can also be described as the belly region of the leaflet) and two sleeve portions 320 that extend outwardly from the body portion 310. The body portion 310 can have a curved bottom edge 330. In some cases, the sleeve portions can be sized and shaped for coupling to anchor elements of the heart valve, such as the anchor elements 160 of FIG. 2.

In use, the prosthetic heart valve 300 provided herein is implanted (e.g., surgically or through transcatheter delivery) in the heart. The edge portions of the leaflets 300 move into coaptation with one another in a closed position to substantially restrict fluid from flowing past prosthetic heart valve in a closed position. The edge portions of the leaflets 300 move away from one another to an open position permitting fluid to flow past the prosthetic heart valve 300. Movement of the leaflets 300 between the closed and open positions can substantially approximate the hemodynamic performance of a healthy natural valve.

As the prosthetic heart valve opens and closes during each heartbeat, each leaflet 300 flexes between an open and a closed position. Tensile and flexural strain on the leaflet 300 can change depending on its position. Leaflets 300 can therefore elongate in various orientations (or directions) as the valve opens and closes. Each leaflet, as shown in FIG. 3A, can elongate in a radial orientation and/or a circumferential orientation with each heartbeat. Leaflets 300 can also elongate in various orientations having an oblique angle relative to the radial and circumferential orientations. Due to the various orientations of elongation that a prosthetic leaflet can experience during use, the leaflet can greatly benefit by being composed of materials with anisotropic physical and mechanical properties.

Figure 3B:
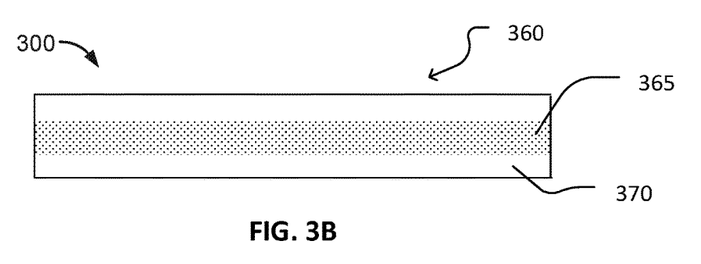
FIG. 3B provides a cross-sectional view of the exemplary leaflet.

FIG. 3B provides a cross-sectional view of the exemplary leaflet 300 provided herein. As shown, leaflet 300 can be made of a composite material 360 having an inner and an outer layer 370. The inner layer 365 can include a plurality of fibers embedded within at least a portion of a polymer matrix. The fibers of the composite material can be composed of one or more fiber materials. The polymer matrix can be disposed in the interior layer as an interpenetrating matrix that partially or fully fills gaps (or space) between individual fibers throughout the entire inner layer 365. The outer layer 460 can be composed of one or more polymer matrix materials.

Figure 4:
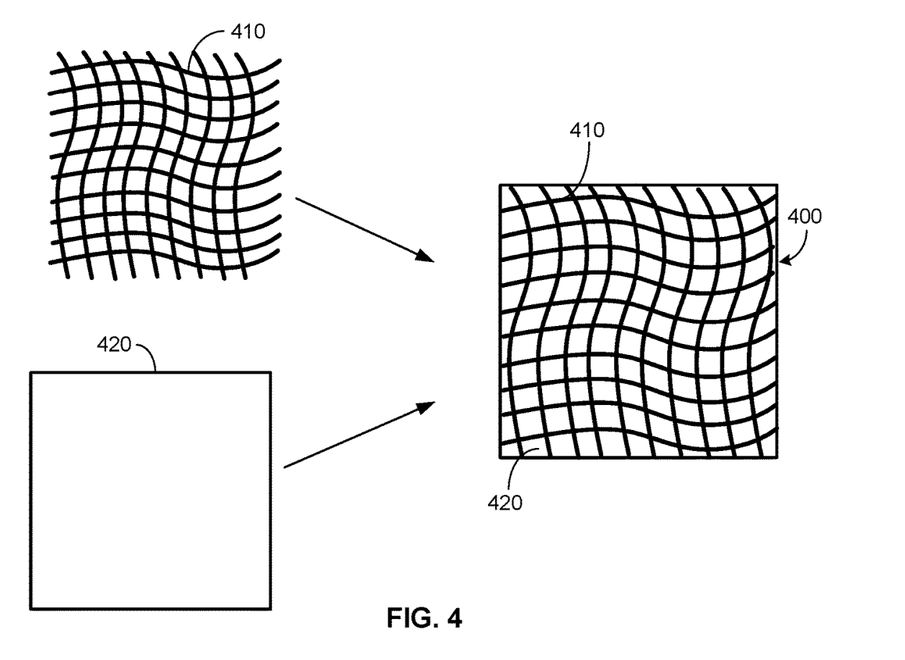
FIG. 4 is a schematic illustration of a composite material provided herein.

FIG. 4 provides a schematic representation of a composite material 400 provided herein. As shown in FIG. 4, composite material 400 can be composed of fibers 410 that are aligned in an ordered pattern to form a woven matrix. In some cases, fibers 410 of composite material 400 can be composed of individual fibers 410 randomly oriented within a polymer matrix 420 to form a non-woven matrix. In some cases, composite material 400 is composed of electrospun fibers. A non-woven fibrous matrix can provide an isotropic material (having the same properties in all directions) while a woven fibrous matrix can produce an anisotropic material (having properties that are directionally dependent).

Still referring to FIG. 4, composite material 400 can include fibers 410 embedded within the polymer matrix 420 in at least one layer (or section) of the composite material, or throughout the entire composite material. In some cases, the composite material 400 can consist of a plurality of fibers 410 and the polymer matrix 420. In some cases, some portions of the composite material 400 can contain fibers 410 and some portions of the composite material 400 can include no fibers 410. In some cases, some portions of the composite material 400 can contain the polymer matrix 420 and some portions of the composite material 400 can include none of the polymer matrix 420. In some cases, the composite material 400 can include additional layers of polymer, which can include different polymers than the polymer in polymer matrix 420 or the same polymer in the polymer matrix 420. In some cases, different layers of polymer can include different polymer fibers 410 and/or different fiber arrangements. In some cases, the composite material 400 can have isotropic properties, which can be due to an arrangement of fibers 410 within matrix 420. In some cases, a heart leaflet can include a composite material 400 having the fibers 410 and polymer matrix 420 throughout the entire composite structure 400 to simplify manufacturing.

Each fiber 410 within the composite material of a leaflet can have an orientation (or direction) for producing desired physical and/or mechanical properties. In some cases, a fiber can have a single orientation such that the fiber extends in one linear direction with respect to an edge of the leaflet, e.g., a free edge along the sleeves 320 as shown in FIG. 3A. In some cases, the fiber can extend in a linear direction that is parallel to an edge of the leaflet. In some cases, the fiber can extend in a linear direction that is oriented at an angle relative to an edge of the leaflet.

Still referring to FIG. 4, each fiber 410 can optionally have a plurality of orientations such that the fiber changes its direction multiple times or continuously. In some case, for example, the fiber 410 with a plurality of orientations can have a non-linear or curved shaped relative to an edge of the leaflet. In some cases, the fiber 410 can be non-linear or curved shaped while the leaflet is in a non-stressed state, but the fiber 410 can become straight when the leaflet in a stressed state. In some cases, the fiber 410 can transition from a curved shape to a straight shape to allow a leaflet to have greater elongation in a direction that is parallel to the fiber orientation and to produce desired anisotropic properties. In some cases, a fiber 410 can have a non-linear shape, such as a curved or curvilinear shape as shown in FIG. 4. In some cases, each fiber 410 can have a repetitive pattern, such as an oscillating, sinusoidal or undulating pattern. For instance, a fiber 410 can include an undulation or a plurality of undulations, in some cases. In some cases, fibers 410 can be straight or have linear shapes. Fibers 410 within the leaflet can be shaped to alter the physical and/or mechanical characteristics of the leaflet material, in various cases. For example, in some cases, sinusoidal fibers or other curved shapes, can produce a leaflet having increased elasticity as compared to leaflets having straight fibers.

In some cases, a single fiber 410 can have different portions with different shapes. For example, a fiber can have a straight portion in one section and a sinusoidal portion in another section. In some cases, a composite material can have one, two, three, four, or more than five sets of fibers, each set having a different shape or pattern. A heart leaflet can be formed with fibers having one or more shapes that provide the leaflet with anisotropic physical and/or mechanical properties. By incorporating fibers with one or more orientations into a leaflet composite material, the properties of the composite material can be directionally tailored to respond to stresses and strains of a pulsating heart.

A heart leaflet can be formed of multiple fiber materials to provide the leaflet with physical and/or mechanical properties of two or more distinct materials. By incorporating layers having different materials with different properties into a leaflet composite material, the properties of the composite material can be tailored, as desired. Multiple layers can be used to form an anisotropic material that optimizes leaflet performance by better mimicking properties of a native heart valve.

An exemplary leaflet provided herein can include a fibrous matrix formed from multiple electrospun fiber materials. The heart leaflet can also be formed of multiple fiber materials to provide the leaflet with physical and mechanical properties of two or more distinct materials.

In some cases, a plurality of fibers can form a layer of fibers within a composite material. In some cases, a single layer of fibers can include more than one material. In some cases, the composite material can include multiple layers of fibers, for example, two, three, four, or greater than five layers of fibers. In some cases, at least one layer of fibers can be made of the same material, for example, a first polymer. In some cases, the different layers of fibers can be made from different materials, e.g., a first layer is made from a first polymer and a second layer is made from a second polymer. Having more than one layer may minimize or prevent tearing and other similar material-related failures from occurring in a heart valve.

Figure 5:
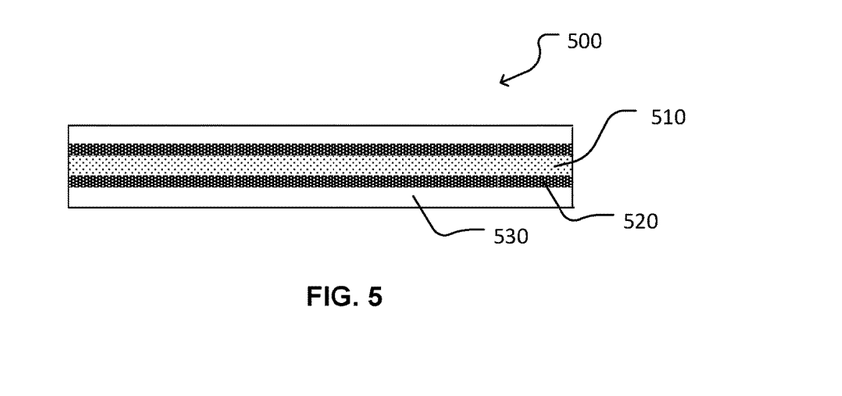
FIG. 5 shows a cross-sectional view of another exemplary leaflet provided herein.

FIG. 5 provides a cross-sectional view of another exemplary composite material 500. The composite material 500 of FIG. 5 includes multiple inner layers 510, 520 and an outer layer 530. The inner layers include an outermost inner layer 520 and an innermost inner layer 510. The outermost inner layer 520 can include a first plurality of fibers and the innermost inner layer 510 can include a second plurality of fibers. The outer layer 530 can be composed of a polymer matrix. In some cases, at least a portion of the fibers of the outermost inner layer 520 can interpenetrate at a portion of the innermost inner layer 510. The outer layer 530, e.g., the polymer matrix, can interpenetrate the outermost inner layer 520 such that the polymer matrix material partially or fully fills spaces between individual fibers of the outermost inner layer 520. In some cases, the material of the outer layer 530, e.g., the polymer matrix material, can interpenetrate both the outermost and innermost inner layers 520, 510.

As shown in FIG. 5, a composite material can have one or more interior fiber layers. In some cases, a composite material can have a fibrous exterior layer. The exterior fibrous layer can provide desired surface modifications to the composite material, for example, provide a surface texture to promote better adhesion properties, eliminate or reduce calcification. The exterior fibrous layer can provide a porous surface for disposing a drug or an antimicrobial agent, in some cases.

An exemplary composite material can include a set of fibers having an orientation (which can also be described as a fiber direction), wherein each of the fibers of the set have the same orientation. In various cases, fiber sets of a leaflet can be oriented to resist straining in a particular direction, as desired. In some cases, one set or layer of fibers can have an orientation that is different than the orientation of another set or layer of fibers within the polymer matrix. In some cases, for example, a first plurality of fibers can have a first orientation and a second plurality of fibers can have a second orientation. In some cases, the first orientation can be different or the same as the second orientation. In some cases, the first and second orientations are generally orthogonal to one another. In some cases, the first and second orientations are generally oblique to one another. In some cases, a composite material can have one, two, three, four, or more than five sets of fibers, each set having a different orientation. A heart leaflet can be formed of fiber sets including multiple orientations that provide the leaflet with anisotropic physical and/or mechanical properties. By incorporating fibers with one or more orientations into a leaflet composite material, the properties of the composite material can be tailored to directionally respond to stresses and strains associated with a pulsating heart.

Fibers of the leaflets described herein can be made of various materials suitable for medical devices and/or implants. The fibers can be made of various biostable and/or biocompatible materials. A biostable material is a material that is resistant to degradation during the use life of a medical device and is not associated with carcinogenicity issues. A biocompatible material is a synthetic or natural material that is not harmful to living tissue. In general, fibers described herein can be composed of polymers, metals (e.g., titanium, stainless steel, tantalum), ceramics (fiberglass, acrylics), or combinations thereof. In some case, fibers are made of thermoplastic polymers, thermoset polymers or combinations thereof. Fibers provided herein can be made of various polymeric materials, such as fluoropolymers, polyurethanes or block copolymers. Suitable polymers for fibers provided herein can be formed from fluoropolymers including, but not limited to, for example, polytetrafluoroethylene (PTFE), polyvinylidene fluoride (PVDF) (e.g. Kynar™ and Solef™), poly(vinylidene fluoride-co-hexafluoropropene) (PVDF-HFP) and combinations thereof. Other suitable fiber polymers can include urethane-based polymers such as polyurethanes, polyurethane elastomers (e.g. Pellethane), polyether-based polyurethanes (e.g. Tecothane), polycarbonate-based polyurethanes (e.g. Bionate and Chronoflex) and combinations thereof. In some cases, other examples of suitable polymer materials for fibers include, but are not limited to, polycarbonates, polyethers, polyesters such as polyethylene terephthalate (PET), polyethylenes, polypropylenes, polyamides (e.g., Kelvar®, Pebax®, nylon 6 and nylon 12), polyetheretherketones (PEEK), polysulfones, polyvinyl alcohols, polyetherimides, polyimide (PI), polybenoxazole (PBO), polybenzothiazole (PBT), polybenzimidazole (PBI), poly-N-phenylbenzimidazole (PPBI), poly-phenylquinoxaline (PPG), poly(p-phenylene terephthalamide) (PPTA), polysulfone, naphtalate based polymer fibers such as polybuthylenenaphtalate (PBN) and polyethylenenaphtalate (PEN), polyhydroquinone-diimidazopyridine (PIPD or also known as M5 fibers) and combinations thereof. In some cases, fibers are formed from block copolymers such as, for example, a poly(styrene-isobutylene-styrene) (SIBS) tri-block polymer and a polyisobutylene urethane copolymer (PIB-PUR).

Figure 6:
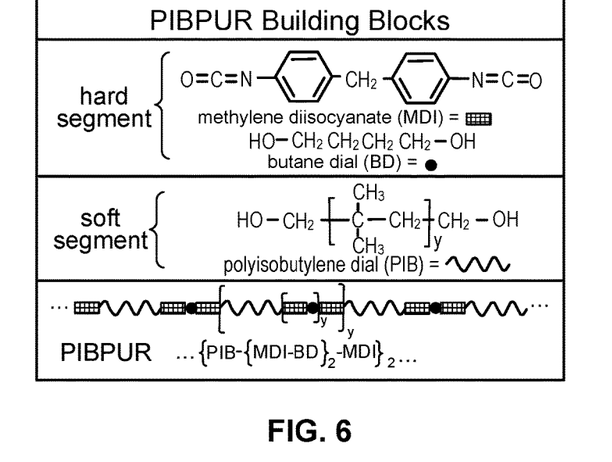
FIG. 6 provides chemical structures for a polyisobutylene urethane copolymer (PIB-PUR) provided herein.

FIG. 6 provides chemical structures for components of a polyisobutylene urethane copolymer (PIB-PUR) used for constructing composite materials provided herein. As shown in FIG. 6, PIB-PUR is composed of soft segment portions and hard segment portions. Polyurethane hard segment portions can include, but are not limited to, methylene diphenyl diisocyanate (MDI), 4,4'-Methylene dicyclohexyl diisocyanate (H12MDI) and hexamethylene (HMDI). Polyurethane soft segment portions can include polyisobutylene macrodiol or polyisobutylene diamine. In some cases, suitable soft segments can include linear, branched or cyclic forms of polyalkene, polyether, a fluorinated polyether, a fluoropolymer, a polyester such as polyethylene terephthalate (PET), a polyacrylate, a polymethacrylate, a polysiloxane, a fluorinated polysiloxane, or a polycarbonate and derivatives thereof. PIB-PUR and PIB-PUR derivatives have the advantages of providing an inert, biocompatible, non-thromobogenic and anti-calcifying material for medical devices and implants.

Fibers of the composite material of leaflet can, in some cases, be made of a liquid crystalline polymer (LCP). LCPs are a special class of aromatic polyester or polyamide copolymers that have semi-crystalline properties due to regions of highly ordered crystalline structures formed therein. LCPs are materials that are generally chemically inert and have a high creep resistance, a high modulus and a high tensile strength. Suitable fiber materials made of LCPs include, but are not limited to, thermotropic polyesters such as Vectran®, poly(p-phenylene terephthalamide) (PPTA), poly(phenylene benzobisoxazole) (PBO), and combinations thereof. Other suitable LCPs can include poly(p-phenylene terephthalamide) such as Kevlar®, Vectran®, Poly(m-phenylene isophthalamide) such as Nomex® and Teijinconex®, Herachron®, Technora®, Twaron®, and Zylon®. In some cases, other high performance fibers can utilized, such as gel-spun ultra-high molecular weight polyethylene (Dyneema® and Spectra®). Benefits of using LCPs include providing leaflets with optionally thinner and smaller dimensions, e.g., thickness or diameter, without compromising mechanical properties of the leaflet, such as tensile strength, or performance characteristics such as robustness and durability. In some cases, diameters of LCP fibers can be as small as 0.5 micrometers (or µm). In some cases, thicknesses of a leaflet composed of LCP fibers can range from about 50 µm to about 100 µm.

In some cases, individual fibers of a composite material can be encapsulated within a jacket (e.g., a polymer jacket) to promote bonding between the fibers and the polymer matrix. In some cases, for example, the leaflet can include LCP fibers that have been encapsulated within a polymer jacket.

Fibers can have diameters or average diameters of at least 1 micron (or 0.00004 inches). Fibers can be, in some cases, in the range of about 1 micron to about 100 microns (or about 0.00004 inches to about 0.004 inches), including all ranges and values therebetween. In some cases, for example, suitable fiber diameter sizes can include ranges of about 1 micron to 5 microns (or about 0.00004 inches to about 0.0002 inches), 5 microns to 10 microns (or 0.0002 inches to about 0.0004 inches), 10 microns to 20 microns (or 0.0004 inches to about 0.0008 inches), 20 microns to 50 microns (or 0.0008 inches to about 0.0020 inches), and 50 microns to 100 microns (or 0.002 inches to about 0.004 inches).). In some cases, fibers can have diameters in the range of about 1 microns to about 10 microns (or 0.0004 inches to about 0.0020 inches), including all ranges and values therebetween. In some cases, the fiber made from polymers can range from about 5 microns to about 100 microns (or 0.00002 inches to about 0.0040 inches), from about 10 microns to about 75 microns (or 0.0004 inches to about 0.003 inches), from about 10 micron to about 50 microns (or 0.0004 inches to about 0.0020 inches), from about 20 microns to about 100 microns (or 0.0008 inches to about 0.0040 inches), from about 25 microns to about 200 microns (or 0.001 inches to about 0.008 inches), or from about 20 microns to about 50 microns (or 0.0008 inches to about 0.002 inches). In some cases, fibers 505, such as LCP fibers, can range from 0.5 microns (or 500 nanometers) to 5 microns (or about 0.00002 inches to about 0.00020 inches).

In some cases, fibers can have diameters or average diameters less than 1 micron, or 1000 nanometers (nm) (or 0.00004 inches). In some cases, fiber diameters or average diameters can range from 1 nm to 1000 nm, including all ranges and values therebetween. For example, fiber diameters can range from about 1 nm to 10 nm, 10 nm to 50 nm, 50 nm to 100 nm, 100 nm to 500 nm, and 500 nm to 1000 nm. In some cases, fiber diameters can range from 100 nm to 1000 nm, including all ranges and values therebetween. Fiber diameter can significantly affect physical and/or mechanical properties of a composite material. In some cases, a suitable fiber diameter can be used to obtain a composite material having certain desired physical and/or mechanical properties. For instance, increasing the fiber diameter of an exemplary composite material can increase the tensile strength of the material.

Fiber density, such as fiber weight percent, within a composite material can vary. In some cases, weight percent of fibers within a composite material can generally range from about 0.1 wt % to about 50 wt %, including all ranges and values therebetween. In some cases, for example, the fiber weight percentage can range from 0.1 to 0.5 wt %, 0.5 to 1 wt %, 1 to 2 wt %, 2 to 3 wt %, 3 to 4 wt %, 4 to 5 wt %, 5 to 10 wt %, 10 to 20 wt %, 20 to 30 wt %, 30 to 50 wt %, 0.5 to 30 wt %, 1 to 20 wt %, 2 to 10 wt %, or 3 to 5 wt %. In some cases, the fiber weight percentage of a composite material can range from about 1 wt % to about 5 wt %. The fiber weight percentage can significantly affect physical and/or mechanical properties of a composite material. In some cases, a suitable fiber weight percentage can be used to customize or adjust the physical and/or mechanical properties of a leaflet material.

Referring back to FIG. 3B, the polymer matrix 470 of the composite material 460 can be disposed within and adjacent to the fibrous matrix 465. The polymer matrix 470 can interpenetrate the fibrous matrix, e.g., at least a portion of the polymer matrix can 470 become disposed between spaces formed between individual fibers that make up the fibrous matrix. The polymer matrix 470 can be made of various biostable and/or biocompatible polymeric materials. In some cases, the polymer matrix can be made of an elastomeric polymer. Suitable polymer matrix materials can include, but are not limited to, homopolymers, copolymers and terpolymers. Various polyurethanes can be used to construct the polymer matrix, such as polyurethanes with soft segments such as polyether, perfluoropolyether, polycarbonate, polyisobutylene, polysiloxane, or combinations thereof.

In some cases, the polymer matrix 470 can be formed from block polymers such as, for example, poly(styrene-isobutylene-styrene) (SIBS) tri-block polymers. Other suitable elastomeric materials include, but are not limited to, silicones, nitrile rubber, fluoroelastomers, polyolephin elastomers, latex-type elastomers, various natural elastomers such as those made from collagen, elastin, cellulose, proteins, carbohydrates, and combinations thereof.

Composite materials can be prepared with various materials and fiber diameters and orientations, such as to improve bond strength, elongation properties, and tensile strengths, in the final composite material. In some cases, electrospun fibers of an exemplary composite material provided herein can have a tensile strength from 20 MPa to 45 MPa, or in some cases at least 49 MPa. In some cases, fibers of a composite material provided herein can have a tensile strength ranging from about 45 MPa to 50 MPa (or 7.1 to 7.25 ksi), 50 MPa to 100 MPa (or 6.5 ksi to 14.5 ksi), 100 MPa to 250 MPa (or 14.5 ksi to 36 ksi), 250 MPa to 500 MPa (36 ksi to 73 ksi), 500 MPa to 1000 MPa (73 ksi to 145 ksi), 1000 MPa to 2000 MPa (145 ksi to 290 ksi), or greater than 2000 MPa (or 290 ksi).

In some cases, polymers of the polymer matrix provided herein can have a tensile strength ranging from about 25 MPa to 30 MPa (or 3.6 ksi to 4.4 ksi), 30 MPa to 40 MPa (or 4.4 ksi to 5.8 ksi), 40 MPa to 50 MPa (or 5.8 ksi to 7.3 ksi), 50 MPa to 60 MPa (or 7.3 ksi to 8.7 ksi), 60 MPa to 70 MPa (or 8.7 ksi to 10 ksi), or greater than 70 MPa (or 10 ksi). In some case, a polymer matrix of an exemplary composite material provided herein has a tensile strength from 20 MPa to 45 MPa, or in some cases about 44 MPa.

In some cases, a polymer matrix of an exemplary composite material provided herein can be made of a polyisobutylene urethane copolymer having a durometer of about 55 D, or from about 60 A to about 55 D shore hardness (or an ultimate tensile strength of about 182 kilopound per square inch (ksi) or 1255 megapascals (MPa)).

An exemplary leaflet composite material provided herein includes a plurality of fibers composed of PIB-PUR described herein and a polymer matrix composed of PVDF-HFP. The PIB-PUR fibrous matrix provides a chemically inert scaffold for the polymer matrix and PVDF-HFP provides a biostable material.

In some cases, a leaflet provided herein can include a plurality of fibers composed of PVDF-HFP and a polymer matrix composed of PIB-PUR described herein. The fibers can form a non-woven or a woven fibrous matrix. The PVDF-HFP fibrous matrix provides a biostable scaffold and the PIB-PUR polymer matrix provides a chemical inert exterior surface for reducing or eliminating calcification in a synthetic leaflet.

In some cases, a prosthetic heart valve leaflet can include a plurality of electrospun fibers at least partially embedded in a polymer matrix. The plurality of fibers can include a first polyisobutylene urethane copolymer (FIB-FUR) having a first predetermined weight average percentage of its hard segment portions. The polymer matrix can include a second polyisobutylene urethane copolymer (FIB-FUR) having a second predetermined weight average percentage of the its hard segment portions. The first predetermined weight average percentage of the hard segment portions can be greater than the second predetermined weight average percentage of the hard segment portions such that the physical and/or mechanical properties of the first and second polyisobutylene urethane copolymer are different.

In some cases, a polyisobutylene urethane copolymer (FIB-FUR) can have a weight average percentage of hard segment portions ranging from about 10 to 90 wt %. In some cases, the high hard segment content includes a weight average percentage ranging between about 60 wt % to about 70 wt %. In some cases, the weight average percentage of the hard segments is between about 60 to 70 wt %. In some cases, the weight average percentage of the hard segment portions is present in the amount of about 30 to 40 wt %. In some cases, the weight average percentage of the hard segments of FIB-FUR can be present in the amount of about 10 to 20 wt %, 20 to 30 wt %, 30 to 40 wt %, 40 to 45 wt %, 45 to 50 wt %, 50 to 55 wt %, 55 to 60 wt %, 60 to 65 wt %, 65 to 70 wt %, 65 to 75 wt %, 75 to 80 wt %, 80 to 85 wt %, 85 to 90 wt %, or greater than 90 wt %.

In some cases, a polyisobutylene urethane copolymer (FIB-FUR) can have a weight average percentage of soft segment (SS) portions present in the amount of about 10 to 90 wt %. In some cases, the weight average percentage of the soft segments is present in the amount of about 40 to 90 wt %. In some cases, the soft segments are present in the amount of about 60 to 70 wt %. In some cases, the weight average percent of the soft segments can range from about 30 wt % to about 40 wt %. In some cases, the soft segments of FIB-FUR can be present in the amount of 40 to 45 wt %, 45 to 50 wt %, 50 to 55 wt %, 55 to 60 wt %, 60 to 65 wt %, 65 to 70 wt %, 65 to 75 wt %, 75 to 80 wt %, 80 to 85 wt %, 85 to 90 wt %, or greater than 90 wt %.

In some cases, a polyisobutylene urethane copolymer has a high hard segment content that includes a weight average percentage of the hard segment portions ranging between about 40 wt % to about 60 wt % and a weight average percent of the soft segment portions of about 40 wt % to about 60 wt %.

In some cases, a polyisobutylene urethane copolymer having low hard segment content includes a weight average percentage of the hard segment portions ranging between about 30 wt % to about 40 wt % and a weight average percent of the soft segment portions of about 60 wt % to about 70 wt %.

Figure 7:
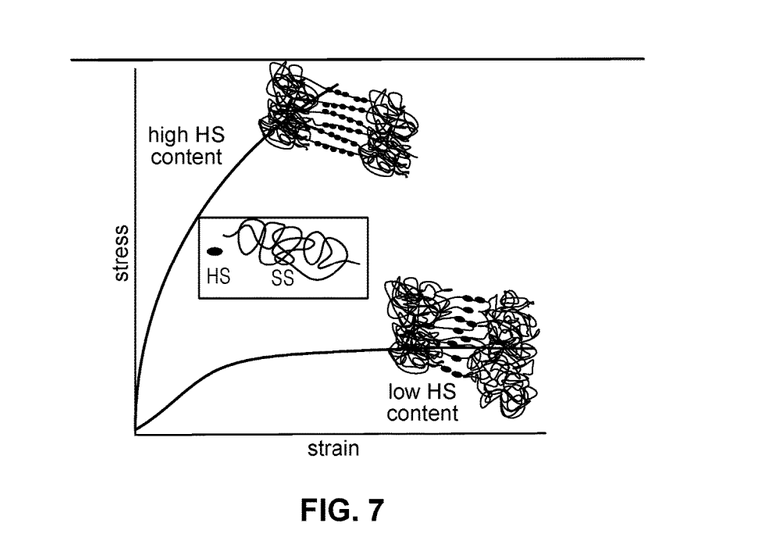
FIG. 7 is a stress-strain curve of composite materials provided herein composed of PIB-PUR having different hard segment content.

FIG. 7 provides an estimated stress-strain curve of composite materials provided herein composed of PIB-PUR with varying hard segment content, illustrating that varying mechanical properties can be achieved by varying the hard segment content of the PIB-PUR. As shown in FIG. 7, a polyisobutylene urethane copolymer having high hard segment content exhibits different mechanical properties than a polyisobutylene urethane copolymer having low hard segment content. More specifically, the polyisobutylene urethane copolymer having high hard segment content exhibits a higher tensile strength and a lower elongation than the polyisobutylene urethane copolymer having low hard segment content. In some cases, decreasing the weight average percentage of hard segment content in a PIB-PUR can decrease tensile strength but increase elasticity of the PIB-PUR.

Exemplary composite materials provided herein can include a hydrogel coating. The hydrogel coating includes a network of hydrophilic polymer chains that can provide the benefit of increasing the hydrophilicity of a surface. In some cases, the composite materials provided herein can have a hydrogel coating that includes polyethylene glycol (PEG) or a PEG derivative, for example, chitosan-PEG, thiol-PEG, maleimide-PEG, amino-PEG, azide-PEG, and carboxyl-PEG, in some cases. Other suitable hydrophilic materials that can be applied to composite materials include, but are not limited to, poly [N-(2-hydroxypropyl) methacrylamide] (PHPMA), poly(vinyl pyrrolidone), polyethylene/oligoethylene, polyHEMA, polytetraglyme, hyalorunic acid, chitosan and derivatives thereof.

Exemplary composite materials provided herein can include an antimicrobial coating, in various cases, to inhibit the growth of harmful microbes within composite materials, thus reducing the risk of infection of potential patients. In some cases, antimicrobial coatings can be surface grafted or covalently attached to a composite material. In some cases, an antimicrobial coating can be a plasma polymerized coating. An exemplary antimicrobial coating, in various cases, can include polyethylene glycol (PEG). In some cases, antimicrobial coatings can be covalently attached to the surface coatings of hydrophilic polymers such as polyethylene glycol (PEG), polyethylene oxide (PEO), polyvinylpyrollidone (PVP), glycosaminoglycans (heparin, hyaluronic acid, etc) and combinations thereof. Other suitable antimicrobial coatings can include, but are not limited to, oxides and salts of graphene, gold and silver. In some cases, the antimicrobial coating can include an anticoagulant agent, for example, heparin and/or heparin derivatives. In some cases, anticoagulant agents can include P2Y12 protein inhibitors such as clopidogrel (Plavix®), ticlopidine (Ticlid®) and prasugrel (Effient®). In some cases, agents can include glycoprotein IIb/IIIa antagonists such as abciximab, eptifibatide and tirofiban. Other suitable anticoagulant agents can include, but are not limited to, bivalirudin (Hirulog®), desirudin (Hirudin®), thrombin inhibitors such as argatroban, aurintricarboxylic acid, polyethylene glycol (PEG), cilostazol and combinations thereof.

In some cases, an outer surface of a composite material can include zwitterionic polymers to reduce the calcification propensity of one or more synthetic materials. In some cases, a zwitterionic polymer includes a backbone with a zwitterionic group (which can also be described as a zwitterionic species or a zwitterionic compound). A zwitterionic group, or a zwitterion (also described as a dipolar ion or an inner salt), is a neutrally charged compound, or molecule, having both a negatively charged ion (anion) and a positively charged ion (cation). In some cases, the zwitterionic polymer can include a zwitterionic pendant group (also described as a side group). In some cases, the zwitterionic polymer can be formed from one or more monomers, wherein the monomer includes a zwitterionic group.

In some cases, a composite material can have a polymer coating that includes polymerized units of a monomer including a zwitterionic group when the polymer coating is exposed to an aqueous environment, in particular blood, at a PH of about 7.4. In some cases, a zwitterionic group of a monomer can be formed by a carboxylic acid group, a sulfonic acid group, or a phosphonic acid group. In some cases, a monomer can include a zwitterionic group composed of an acrylate, a methacrylate, an acrylamide, or a methacrylamide. In some cases, a cation of a zwitterionic group can be formed by an (cyclo)aliphatic or aromatic amine, an amidine, or a guanidine. In some cases, a cation of a zwitterionic group can be a quaternary amine.

In some cases, a cation and an anion of a zwitterionic group can be part of the same pendant group of the monomer unit. In some cases, the pendant group has the structure formula: X—$(CH_2)_n$—$N+R_2$—$(CH_2)_m$—Y or X—$(CH_2)_n$—O—P(O—)—$(CH2)_m$-Z, wherein:

X is the point of covalent attachment to the repeat unit of the monomer;

each R is independently selected from C1- to C4-alkyl, in particular methyl;

n and m are each integers between 1 and 8;

Y is a anionic group selected from COO—, $SO_3$—, O—SO3-, O—PO3-, and PO3-; and

Z is a cationic group derived from a (cyclo)aliphatic or aromatic amine, an amidine, a guanidine, or a quaternary amine, in particular NR'3+, wherein each R' is independently selected from C1- to C4-alkyl, in particular methyl.

Zwitterionic polymers can generally minimize or prevent biological responses normally caused by synthetic materials implanted in a body by creating a water-saturated surface that generally inhibits protein adsorption. Benefits of using zwitterionic polymeric surfaces include increasing the hydrophilicity, nonspecific protein adsorption resistance and/or platelet adhesion resistance of synthetic surfaces.

Figure 8:
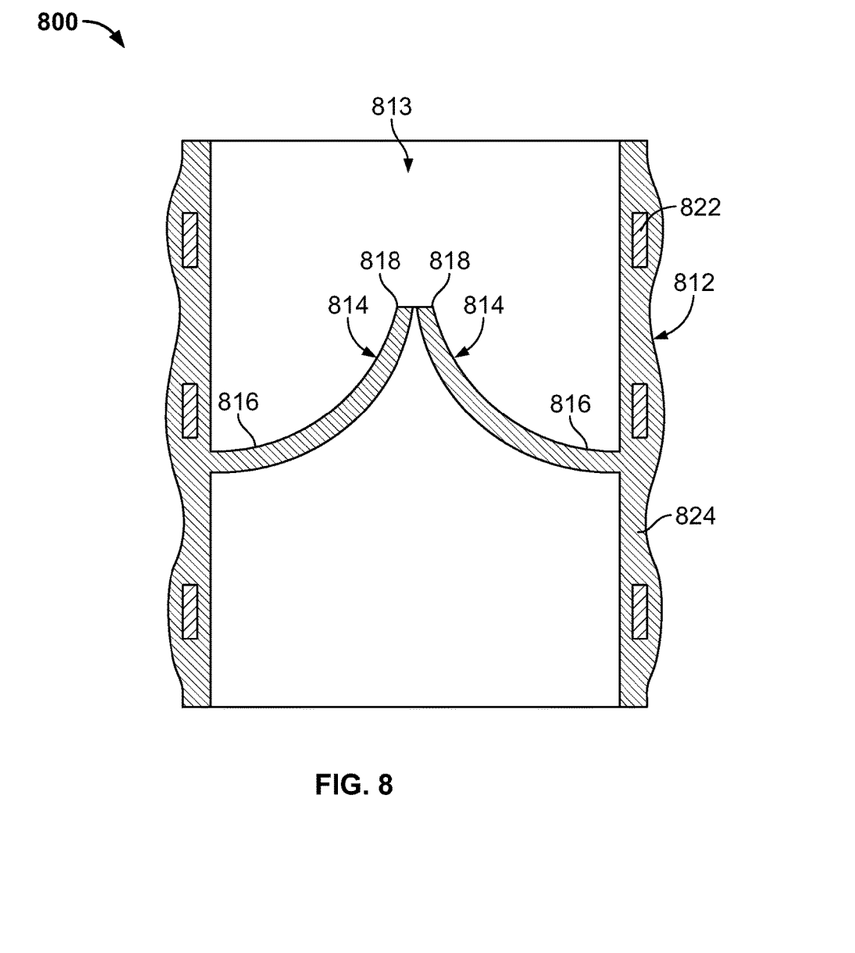
FIG. 8 is an illustration of another exemplary prosthetic heart valve provided herein.

FIG. 8 provides another embodiment of an artificial heart valve 800. Prosthetic heart valve 800 includes a base 812 defining a substantially cylindrical passage 813 and a plurality of polymeric leaflets 814 disposed along the substantially cylindrical passage 813. Each polymeric leaflet 814 includes a respective root portion 816 coupled to base 812 and a respective edge portion 818 movable relative to the root portion 816 to coapt with the edge portions of the other polymeric leaflets along a coaptation region. In some cases, the entire heart valve 800 can be made of a composite material provided herein. In some cases, portions of heart valve 800, e.g., the polymeric leaflets 814 of the heart valve 800, can be made of a composite material provided herein. In some cases, the polymeric leaflets 814 can include a plurality of fibers provided herein. In some cases, the plurality of fibers 814 can include a plurality of undulations to provide the leaflet with multi-stage elastic properties.

Base 812 includes a frame 822 disposed in a polymer layer 824. The polymer layer 824 can be composed of composite materials provided herein. In some cases, polymer layer 824 can include a plurality of fibers 814 in which each fiber optionally includes a plurality of undulations. Polymer layer 824 secures respective root portions 816 of polymeric leaflets 814 to the base 812. Polymer layer 824 can form a substantially continuous surface with respective root portions 816 of polymeric leaflets 814. This can reduce the likelihood of stress concentrations at the junction of respective root portions 816 and base 812. Additionally or alternatively, polymer layer 824 can be disposed between each of polymeric leaflets 814 and frame 822 such that polymer layer 824 protects polymeric leaflets 814 from inadvertent contact with frame 822 (e.g., as can occur through eccentric deformation of prosthetic heart valve 800 on a calcium deposit present at the implantation site).

In some cases, frame 822 is substantially cylindrical such that the outer surface of the base 812 is substantially cylindrical and the polymer layer 824 disposed on the frame 822 forms the substantially cylindrical passage 813. In some cases, frame 822 is completely disposed in the polymer layer 824, with the polymer layer 824 forming a contoured outer surface of the valve 800. In some cases, the frame 822 is partially disposed in the polymer layer 824. In some cases, the polymer layer 824 is applied to the frame 822 to form a substantially smooth inner and/or outer surface of the valve 800.

Methods of Manufacturing

Methods provided herein can be used to form a medical device, such as a prosthetic heart valve leaflet described herein, made of one or more composite materials. In particular, the methods provided herein can be used to form a leaflet with at least one of the composite materials described herein having multi-stage elastic properties. In some cases, the method of forming a leaflet includes disposing a first polymeric layer on a mandrel. In some cases, the method of forming a leaflet includes disposing a plurality of fibers having a plurality of undulations on the first polymeric layer discussed herein. In some cases, the method of forming a leaflet includes disposing a second polymeric layer on the plurality of fibers discussed herein.

Various methods can be used to form a composite material provided herein. Suitable methods for forming at least a portion of the composite material include, but are not limited to, compression molding, extrusion, solvent casting, injection molding, electrospinning, force spinning, melt-blowing, and combinations thereof. Examples of other methods for partially or fully constructing a part composed of a composite material also include, but are not limited to, dip coating, roll coating, spray coating, flow coating, electrostatic spraying, plasma spraying, spin coating, curtain coating, silkscreen coating, and combinations thereof. In some cases, the processes described herein can be used to form fibers and/or a polymer matrix. In some cases, the processes described herein can be used fabricate reinforced leaflets that incorporate a performed mesh composed of aligned or nonaligned fibers. For example, in some cases, a composite material can be constructed by laying fibers into a compression mold that disposes a polymer matrix into and onto the fibers.

Compression molding can be used to produce sheets or molded parts composed of a composite material. The compression molding process is a process of forming a part by placing a preformed polymeric material, such as a preformed thermoset compound, directly into a heated metallic mold. The preformed thermoset compound conforms to the shape of the mold as it becomes pliable and compressed by the heated mold. In some cases, a composite material can be made by inserting one or more preformed compounds and/or one or more fibrous matrixes into a compression mold.

Extrusion and injection molding can be used to form at least a portion of a part composed of composite materials, in some cases. Extrusion is a process of forming parts with a fixed cross-section profile by pushing or pulling a material through a die having a desired cross-section. Injection molding is a process that feeds one or more heated materials into a mold cavity and cools the materials in the shape of the cavity. Either of these processes can be used to form a composite material substrate before or after incorporating a layer of fibers.

Solvent casting is another process that can be used to form a composite material. This process involves dissolving a polymer material in an organic solvent, casting the solution in a mold and drying the solvent to create a final structure. In some cases, a second material, such as particles or fibers, can be added to the solution prior to casting to form composite structures composed of the second material embedded within the polymer material. In some cases, the second material can be a dissolvable material, e.g., a dissolvable salt, which results in a porous structure.

Various methods can be employed to form fibers of a leaflet composed of a composite material. Examples of some suitable methods can include, but are not limited to, electrospinning, force spinning and melt-blowing processes. Electrospinning, force spinning and melt-blowing processes are exemplary processes that can be used to form fibers of a composite material. Electrospinning is a process that uses electrical charge to create fibers from a liquid while force spinning is a process that uses centrifugal force to create fibers. Melt-blowing is a process in which a molten thermoplastic resin is extruded through a die and then stretched and cooled with high-velocity air to form long, fine fibers. Both electrospinning and melt-blowing processes can be used to form fibers into a woven or a non-woven fibrous matrix. In some cases, multiple fiber materials can be formed simultaneously by one or more apparatuses.

Various methods can be used for incorporating fibers into a polymer matrix to adequately bond fibers within a polymer matrix. Methods described herein can be used to clean and/or surface modify fibers, encapsulate fibers in a jacket (e.g., a polymer jacket), deposit fibers into a mesh pattern of a leaflet, and coat a fibrous matrix with a polymer solution.

In some cases, fibers can be formed prior to being deposited onto a polymer matrix. In particular, preformed fibers can be deposited and oriented as desired into a mesh pattern in the shape of a valve leaflet. Fibers can be oriented to optimize physical and/or mechanical properties and allow for different degrees of elongation in different directions, if desired. In some cases, fibers can be deposited directly onto a target surface, e.g., a polymer matrix surface. Fibers can be deposited onto a target surface using methods described herein to create a non-woven matrix or a woven fibrous matrix.

Individual fibers of a composite material can be optionally encapsulated in a jacket (e.g., a polymer jacket) to promote bonding and reduce the risk of fibers being released from a polymer matrix. In some cases, individual fibers can be encapsulated in a polymer jacket with a conformal coating by using a solution process, such as spray coating or dip coating. In some cases, fiber encapsulation can be facilitated using a reactive process to promote covalent bonding between a fiber and a polymer jacket. An exemplary reactive process can include coating a fiber with a primer solution of diisocyanate, such as monomers or low molecular weight oligomers of methylene diphenyl diisocyanate (MDI), curing the diisocyanate to the fiber surface, and applying over the coated fiber a reactive layer of hydroxyl terminated oligomer or amine terminated oligomers. In some cases, the reactive layer of hydroxyl terminated oligomer or amine terminated oligomers can be applied to a fiber without adding a diisocyanate coating.

Fibers can be encapsulated in a jacket (e.g., a polymer jacket) before or after being deposited onto the target surface. In the latter case, fibers can be coated with a polymer solution once formed and oriented as desired on a target surface. The polymer solution applied to the fibers can be a reactive or a non-reactive polymer solution. Residual solvents that might be present in the resultant polymer coated fiber can be minimized or removed by using appropriate solvents, heating, filtering and/or drying the composite material.

At least a portion of a composite material can undergo surface processing to optimize certain surface characteristics, such as hydrophilicity or calcification propensity. Surface processing can be used to clean, activate, neutralize a surface, and/or realign fiber orientation in a fibrous matrix. In some cases, surface processing can be utilized before or after a coating application, such as a hydrogel coating application. In some cases, surface processing may occur before a coating application to change the surface characteristic of a material to facilitate improving covalent bonding between the material surface and the coating. In some cases, surface processing can occur after a coating application to further enhance certain properties of the coating. In some examples, surface processing includes, but is not limited to, plasma treating, corona treating, acid etching and vacuum plasma treating.

Plasma treating is a surface modification process that uses ionized gas molecules to alter the surface characteristics of a polymeric material. Plasma treatment can remove volatile organic compounds from the polymeric material. Plasma treatment can be used to activate the surface of a polymeric material that does not typically bond easily, or exhibits hydrophobic characteristics. In some cases, plasma treating may be used to temporarily activate the surface of a composite material, e.g., a fibrous matrix, before another material, e.g., a hydrogel, is applied. Plasma treating can be used to enhance interfacial adhesion between a material such as a hydrogel and a matrix material. For example, plasma treatment can be applied to a PIB-PUR matrix described herein prior to a polyethylene glycol (PEG) coating application. Plasma treating can provide the benefit of removing potential contaminants from a surface, modifying surface topography, as desired, and/or enhancing interfacial adhesion between at least two materials, for example, a coating and a matrix polymer of a composite material.

In some cases, fibers can be cleaned and/or surface modified to enhance adhesion of the fibers to another polymeric material, e.g. a polymer matrix or polymeric jacket. Suitable methods for cleaning and/or surface modifying fibers include processes provided herein, e.g., plasma treating. Cleaning and surface modification processes can be applied to fibers before or after the fibers have been added to a target surface.

Composite materials provided herein can be coated with hydrophilic coatings and/or antimicrobial coatings using known coating techniques, such as dip coating, spray coating, brush coating, roller coating, etc.

A number of embodiments of devices, systems, and methods have been described herein. Nevertheless, it will be understood that various modifications may be made without departing from the spirit and scope of the subject matter described herein. Accordingly, other embodiments are within the scope of the following claims.

What is claimed is:

1. A prosthetic heart valve leaflet comprising a composite material, the composite material comprising:
   a plurality of electrospun fibers at least partially embedded in a polymer matrix, the plurality of electrospun fibers comprising a first polyisobutylene urethane block copolymer comprising hard and soft segment portions, having a first predetermined weight average percentage of hard segment portions and the polymer matrix comprising a second polyisobutylene urethane block copolymer comprising hard and soft segment portions, having a second predetermined weight average percentage of hard segment portions, wherein the first predetermined weight average percentage of the hard segment portions is greater than the second predetermined weight average percentage of the hard segment portions.

2. The prosthetic heart valve leaflet of claim 1, wherein the hard segment portions of the first and second polyisobutylene urethane block copolymers are prepared from a methylene diisocyanate and a butane diol.

3. The prosthetic heart valve leaflet of claim 1, wherein the first and second polyisobutylene urethane block copolymers comprise soft segment portions, wherein the soft segment portions are prepared from a residual monomer of a polyisobutylene diol or a polyisobutylene diamine.

4. The prosthetic heart valve leaflet of claim 3, wherein the soft segment portions further include at least one selected from the group consisting of a polyether, a fluorinated polyether, a fluoropolymer, a polyester, a polyacrylate, a polymethacrylate, a polysiloxane, a fluorinated polysiloxane, or a polycarbonate.

5. The prosthetic heart valve leaflet of claim 3, wherein the first polyisobutylene urethane block copolymer comprises a weight average percentage of the hard segment ranging between 40 wt % to 60 wt % and a weight average percent of the soft segment of 40 wt % to 60 wt %.

6. The prosthetic heart valve leaflet of claim 3, wherein the second polyisobutylene urethane block copolymer comprises a weight average percentage of the hard segment ranging between 30 wt % to 40 wt % and a weight average percent of the soft segment of 60 wt % to 70 wt %.

7. The prosthetic heart valve leaflet of claim 1, further comprising a hydrogel coating disposed on the composite material.

8. The prosthetic heart valve leaflet of claim 7, wherein the hydrogel coating includes polyethylene glycol (PEG).

9. The prosthetic heart valve leaflet of claim 1, wherein a first portion of the plurality of electrospun fibers have a first predetermined orientation and a second portion of the plurality of electrospun fibers have a second predetermined orientation.

10. The prosthetic heart valve leaflet of claim 1, wherein the first polyisobutylene urethane block copolymer and the second polyisobutylene block copolymer both comprise hard segment portions, wherein individual hard segment portions are made from a methylene diisocyanate (MDI) and a butane diol (BD).

11. The prosthetic heart valve leaflet of claim 10, wherein the first and second polyisobutylene urethane block copolymers are made using a mole ratio of MDI/(BD+soft segments) of 1.

\* \* \* \* \*